United States Patent [19]

Lindemann et al.

[11] 4,372,869
[45] Feb. 8, 1983

[54] DETERGENT COMPOSITIONS

[75] Inventors: Martin K. O. Lindemann, Bridgewater; Elvin R. Lukenbach, Somerset; Robert J. Verdicchio, Succasunna, all of N.J.

[73] Assignee: Johnson & Johnson Baby Products Company, New Brunswick, N.J.

[21] Appl. No.: 263,954

[22] Filed: May 15, 1981

[51] Int. Cl.$^3$ .............................................. C11D 17/00
[52] U.S. Cl. .............................. 252/174.16; 252/526; 252/527; 252/528; 252/545; 252/DIG. 7; 252/DIG. 13; 260/403; 260/924; 260/926; 260/943; 260/944; 260/945
[58] Field of Search ............... 252/174.16, 545, 526, 252/546, 527, 528, DIG. 7, DIG. 13; 260/926, 924, 944, 943, 403, 945

[56] References Cited

U.S. PATENT DOCUMENTS

| | | | |
|---|---|---|---|
| 3,310,496 | 3/1967 | Mansfield et al. | 252/545 |
| 3,405,168 | 10/1968 | Kowalski et al. | 252/545 |
| 3,940,423 | 2/1976 | Eibl et al. | 252/545 |
| 4,215,064 | 7/1980 | Lindemann et al. | 260/403 |
| 4,231,903 | 11/1980 | Lindemann et al. | 252/545 |
| 4,233,192 | 11/1980 | Lindemann et al. | 252/545 |
| 4,261,911 | 4/1981 | Lindemann et al. | 260/403 |

*Primary Examiner*—Michael R. Lusignan
*Assistant Examiner*—Janyce A. Bell
*Attorney, Agent, or Firm*—Steven P. Berman

[57] ABSTRACT

Detergent and cleansing compositions are provided containing a pyrophosphobetaine compound and preferably at least one other surfactant.

7 Claims, No Drawings

DETERGENT COMPOSITIONS

BACKGROUND OF THE INVENTION

The present invention relates to detergent and cleansing compositions, and more particularly to those detergent and cleansing compositions which have relatively low ocular irritation and yet exhibit good foam volume and improved foam stability.

Detergent and cleansing compositions, like most types of cleaning agents, generally comprise a mixture of one or more surfactants as the active ingredient, as well as builders, perfumes, coloring agents, thickeners, and the like. The surfactant molecules have two or more different moieties comprising: (1) a hydrophobic hydrocarbon chain miscible with organic materials and (2) a hydrophilic moiety miscible with water. Surfactants of this type solubilize fat soluble soils via a complex adsorption/emulsification mechanism. This process allows the efficient removal of soil from the body. The surfactants may be classified as anionic, cationic, nonionic or amphoteric depending upon the nature of the hydrophile.

It is desirable that detergent and cleansing compositions have good foam volume and good foam stability, particularly if they are to be used as shampoos. The amount of foam generated by a shampoo composition has a direct bearing on the perceived efficiency with which it cleans the hair. The stability of the foam generated provides an indication to the user as to how long it will keep the hair lathered. Generally speaking, the greater the volume of foam produced and the more stable the foam, the more efficient the perceived cleansing action of the shampoo. In addition, other detergent and cleansing compositions, such as liquid skin cleansers andd baby bath compositions, are enhanced by high foam volume and good foam stability.

Furthermore, it is essential that products of this type and in particular a shampoo recommended for use on infants and/or children have low ocular irritation and sting potential.

In the prior art, attempts to achieve such low ocular irritating compositions have been described such as by Masci et al. in U.S. Pat. No. 3,055,836 and Bolich et al. in U.S. Pat. No. 3,928,251. Such compositions have contained either an amphoteric/anionic reaction product or a betaine/sultaine-anionic blend in combination with an ethoxylated nonionic, but such formulations have generally exhibited inferior foam volume and stability when compared to traditional shampoo formulations.

A recently issued patent to Lindemann et al, U.S. Pat. No. 4,233,192, discloses low irritating compositions containing phosphobetaines and/or phosphitaines alone or in combination with other surfactants. These phosphobetaines and phosphitaines are amphoteric and zwitterionic surfactants having at least one phosphorus containing anion in the molecule and are described in U.S. Pat. Nos. 4,215,064 and 4,261,911 respectively.

It has now been discovered that the aforementioned deficiencies are readily and unexpectedly overcome while maintaining a low level of irritancy by utilizing a novel class of amphoteric and zwitterionic betaine surfactants, so-called "pyrophosphobetaines." These pyrophosphobetaines are amphoteric and zwitterionic surfactants having at least one anion having a phosphorus-oxygen-phosphorus bond in the molecule as described in copending U.S. Pat. application Ser. No. 263,959 filed May 15, 1981.

It is thus an object of the present invention to prepare detergent and cleanser compositions which are effective for personal cleansing of the skin and hair.

It is another object of the present invention to provide detergent and cleansing compositions which provide good foam volume and good foam stability.

It is yet a further object of the present invention to provide detergent and cleansing compositions which, while being effective cleansing agents for the skin and hair, exhibit low irritancy.

These and other objects of the present invention will become apparent to one skilled in the art from the detailed description given hereinafter.

SUMMARY OF THE INVENTION

This invention encompasses detergent and cleaning compositions comprising as the active ingredient a pyrophosphobetaine surfactant, and preferably at least one other surfactant selected from the group consisting of anionic, nonionic, cationic and amphoteric detergents. The balance of the compositions can comprise various detergency and cleansing adjuncts, fillers, carriers and the like well known in the art.

DETAILED DESCRIPTION OF THE INVENTION

The detergent and cleansing compositions of the present invention comprise as the active ingredient a pyrophosphobetaine and preferably at least one other surfactant.

The pyrophosphobetaines which are useful in the present invention are novel compounds described and claimed in copending patent application Ser. No. 263,959, filled May 15, 1981 and are characterized as amphoteric and zwitterionic betaine compounds containing at least one anion having a phosphorus-oxygen-phosphorus bond.

The pyrophosphobetaines are of the formula

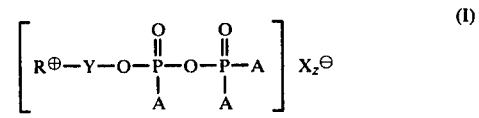

wherein:
A is selected from —O⁻,—OM and —O—Y—R+ with the proviso that at least one A is —O—;
X⁻ is an anion;
z is an integer from 0 to 3, a value necessary for charge balance;
R is an amine or amidoamine moiety of the formula

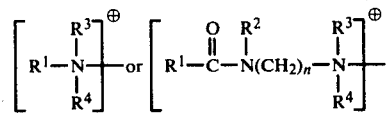

wherein:
R¹ is alkyl, alkenyl, alkoxy, or hydroxyalkyl of from 5 to 22 carbon atoms each, or alkyl or alkaryl of up to 20 carbon atoms;
R² is hydrogen or alkyl, hydroxyalkyl or alkenyl of up to 6 carbon atoms each or cycloalkyl or up to 6 carbon atoms, preferably of from 2 to 5 carbon atoms, or polyoxyalkalene of up to 10 carbon atoms;

$R^3$ and $R^4$, which may be the same or different, are selected from alkyl, hydroxyalkyl, carboxyalkyl of up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, e.g., a morpholino structure, in which the Y radical is bonded to a ring atom of said N-heterocycle other than the nitrogen of the R moiety;

n is an integer from 2 to 12;

Y may be alkylene, optionally interrupted by up to 3 oxygen atoms, of up to 12 carbon atoms, which alkylene chain may optionally be substituted with lower alkyl, alkoxy, hydroxy or hydroxyalkyl, e.g., of not more than 10 carbon atoms each;

M is hydrogen, an organic radical selected from alkyl or hydroxyalky of up to 6 carbon atoms, polyhydroxyalkyl of up to 10 carbon atoms, glyceryl, cycloalkyl of up to 6 carbon atoms, aryl or arylalkyl of up to 10 carbon atoms, or a salt radical selected from alkali metals (e.g., sodium, potassium or ammonium and substituted ammonium radicals), and alkaline earth metals (e.g., magnesium or calcium).

The term "polyoxyalkalene" as used above in the definition of $R^2$, $R^3$ and $R^4$ may be of the formula ($R^5$—O—$R^{5'}$), wherein $R^5$ and $R^{5'}$, are alkyl of from 1 to 4 carbon atoms and m is an integer from about 2 to 10.

The pyrophosphobetaine compounds described above can be prepared in accordance with the processes described in copending application Ser. No. 263,959, filed 5/15/81, the teachings of which are incorporated herein by reference.

Representative pyrophosphobetaine compounds useful in the present invention include compounds having the following structures:

(Compound AA)
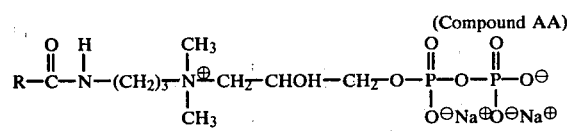

wherein R is a mixture of $C_{11}H_{23}$ and $C_{13}H_{27}$ (Compound BB)
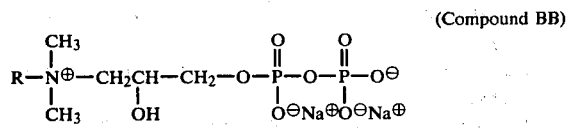

wherein R is a mixture of $C_{11}H_{23}$—$C_{17}H_{35}$

The pyrophosphobetaine compounds can be present in the detergent and cleansing compositions of the present invention in a range of from about 1.0 to 20.0% by weight of the total composition, preferably from about 3.0 to 7.0% by weight of the total composition.

Preferred embodiments of the present invention relate to detergent and cleansing compositions containing a pyrophosphobetaine and at least one other surfactant selected from the group consisting of amphoteric, nonionic, anionic and cationic detergents.

The amphoteric surfactants which may be used in the present invention include betaines, sultaines, phosphobetaines, phosphitaines and n-alkylamino propionates and n-alkylimino dipropionates. The betaine and sultaine surfactants useful in this invention are described in U.S. Pat. No. 3,950,417, and the phosphobetaines and phosphitaines are described in U.S. Pat. Nos. 4,215,064 and 4,261,911. The n-alkylamino propionates and n-alkylimino dipropionates are sold under the tradename Deriphats by General Mills.

The preferred betaine amphoteric surfactants include the alkylbetaines such as cocodimethylcarboxymethylbetaine, lauryldimethylcarboxymethyl betaine, lauryldimethylalpha-carboxymethylbetaine, cetyldimethyl carboxymethylbetaine, lauryl-bis-(2-hydroxyethyl) carboxymethylbetaine, oleyldimethyl-gamma-carboxypropylbetaine, lauryl-bis (2-hydroxypropyl) alpha-carboxyethylbetaine, and the like; the sultaines such as cocodimethylpropylsultaine, stearyldimethylpropylsultaine, lauryl-bis-(2-hydroxyethyl) propylsultaine and the like, and the amidosultaines such as cocoamidodimethylpropylsultaine, stearylamidodimethylpropylsultaine, laurylamido-bis-(2-hydroxyethyl) propylsultaine; the phosphobetaines and phosphitaines such as those of the following structures:

(a)
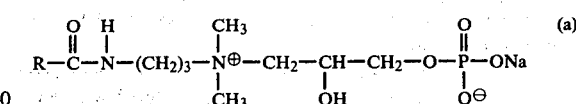

(b)
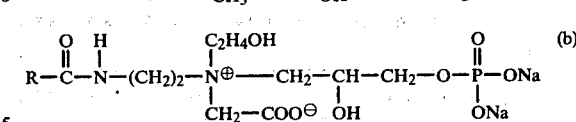

(c)
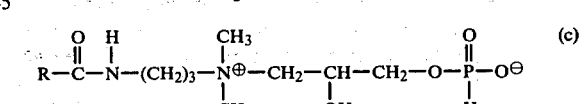

(d)
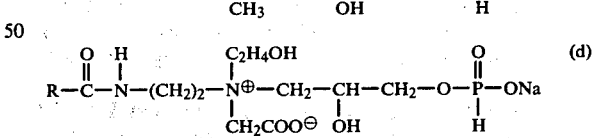

wherein R is $C_8$-$C_{22}$ and mixtures thereof.

(Compound CC)
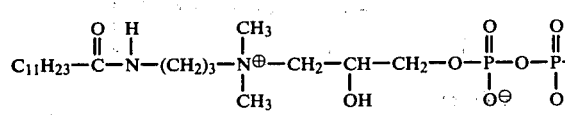

(Compound DD)
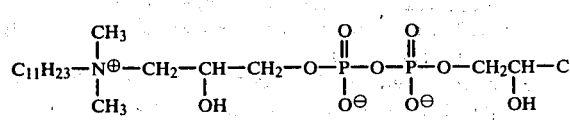

The preferred n-alkylamino propionates and n-alkylimino dipropionates include those of the following structures:

$$R-N^{\oplus}H_2-CH_2-CH_2-COO^{\ominus}$$ and

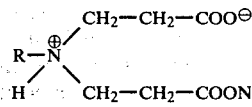

wherein R is from about 8 to 22 carbon atoms and mixtures thereof. The amphoteric detergents should be present in an amount from about 1 to 20% by weight of the total composition.

It is envisioned that any anionic surfactant may be used in the compositions of the invention such as, for example, an alkyl sulfate of the formula $R-CH_2-OSO_3X$, an alkylether sulfate of the formula $R(OCH_2CH_2)_p-OSO_3X$, an alkylmonoglyceryl ether sulfonate of the formula

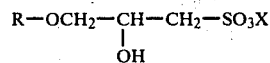

an alkylmonoglyceride sulfate of the formula

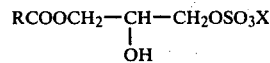

an alkylmonoglyceride sulfonate of the formula

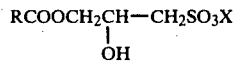

an alkyl sulfonate of the formula $RSO_3X$, an alkylaryl sulfonate of the formula

an alkyl sulfosuccinate of the formula

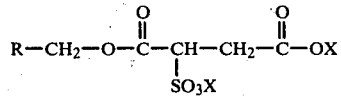

an alkyl sarcosinate of the formula

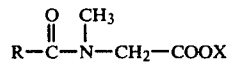

an acyl isathionate of the formula

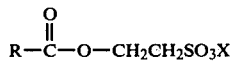

an alkyl methyl tauride of the formula

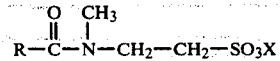

a fatty acid protein condensate of the formula

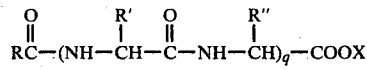

an alcohol ether carboxylate of the formula $RO(CH_2CH_2O)_r-CH_2CO_2X$ and the like;

wherein:
R is higher alkyl having 7 to 17 carbon atoms:
R' and R" are each selected from the group consisting of hydrogen, loweralkyl, hydroxyloweralkyl, thioloweralkyl, carboxyloweralkyl, aminoloweralkyl, benzyl, and p-hydroxybenzyl;
X is selected from the group consisting of alkali metal ions, alkaline earth metal ions, ammonium ions, and ammonium ions substituted with from 1 to 3 loweralkyls;
p is an integer from about 3 to about 6;
q is an integer from 2 to about 6 and r is an integer from 2 to 10.

The preferred type of anionic surfactant is an alkyl ether sulfate, more preferably sodium tridecyl-alcohol ether sulfate in which p is 1 to 5. The anionic detergent should be present in an amount of from about 1 to 20% by weight of the total composition.

Nonionic detergents which are useful include the alkylene oxide ethers of phenols, fatty alcohols, and alkyl mercaptans; the alkylene oxide esters of fatty acid amides; the condensation products of ethylene oxide with partial fatty acid esters, and mixtures thereof. The polyoxyalkylene chain in such agents may contain from 5 to 100 alkylene oxide units in which each alkylene unit has from 2 to 3 carbon atoms.

The preferred nonionic surfactnat in the compositions of the invention is a water-soluble polyoxyethylene derivative of a hydrophobic base, said derivative being a member of the group consisting of the reaction products of 9-20 carbon atom fatty acid monoesters of aliphatic polyhydric alcohols, which polyhydric alcohols contain at least 3 hydroxyls, with at least 10 moles of ethylene oxide, and preferably with from about 10 to about 100 moles of ethylene oxide.

The nonionic surfactant should be present in an amount of from about 1 to 20% by weight of the total composition.

Cationic surfactants suitable in these compositions include mono- and bis-quaternary ammonium halides such as stearyldimethylbenzylammonium chloride, cetyltrimethylammonium chloride, N,N-dioctadecyl-N,N,N',N'-tetramethyl-1,5 (3-oxapentylene) diammonium dibromide; tertiary amine salts such as cocamidopropyl dimethylamine hydrochloride; stearylamidopropyldimethylamine citrate; cationic polymers such as hydroxyethyl cellulose reacted with epichlorohydrin and then quaternized with trimethylamine. (Polymers of this type are sold by Union Carbide under the tradename Polymer JR.) The cationic surfactants should be present in an amount of from about 1 to 5% by weight of the total composition.

The total amount of the active surfactant ingredients in the present invention should not be greater than about 35% by weight of the total composition in order to avoid ocular irritation problems, preferably from about 8 to 15% by weight of the total composition.

In addition, other ingredients conventionally added to detergent and cleansing compositions for personal use, such as dyes, preservatives, perfumes, thickeners, opacifiers, conditioners, emollients, buffering agents, and the like, may be added in minor amounts. Ingredients such as dyes, preservatives and perfumes together usually constitute less than 2% by weight of the total composition and thickeners may be added to the composition in an amount of from about 1 to about 3% by weight of the total composition.

The detergent and cleansing compositions of the present invention may be concentrate compositions which are subsequently modified by dilution with water or other diluents to provide the ultimate compositions for use or they may be the ultimate cleansing compositions to be employed without modification. The compositions of the present invention are primarily useful in shampoo formulations where high foaming characteristics as well as low ocular and skin irritation potential are desired. They may also be used as liquid soaps and cleansers such as baby bath compositions, in bubble bath compositions, as well as in compositions suitable for cleansing animals and inanimate objects.

The aforementioned detergent and cleansing compositions are prepared by admixing the pyrophosphobetaine with the other surfactant(s), if utilized, at room temperature or slightly elevated temperatures (about 50° C.) and then sufficient deionized water is added to bring the composition to about three-quarters of its intended weight. The pH is adjusted to within the range of 5 to 8, by adding strong acid, e.g., HCL, or strong base, e.g., NaOH, as needed. Other ingredients such as viscosity builders, preservatives, dyes, perfumes and the like are incorporated prior to adjusting the pH and adding the remainder of the water.

The detergent and cleansing compositions of the present invention can be tested for ocular irritation by the following modified Draize Test (J. H. Draize et al., Toilet Goods Assn. No. 17, May 1952, No. 1. Proc. Sci. Sect.).

A 0.1 ml sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

The detergent and cleansing compositions of the invention provide high foam volume and moreover outstanding foam stability as measured by an adaption of the well-known Ross-Miles foam test principle ["Oil and Soap" 18.99–102(1941)1]:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin-dioxane solution which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the detergent and cleansing compositions prepared in accordance with the present invention are illustrated by the following representative examples. It will be understood, however, that the invention is not confined to the specific limitations set forth in the individual examples, but rather to the scope of the appended claims.

EXAMPLE I

A liquid cleansing composition is prepared by charging 2.5 grams of Polymer JR and 300 grams of deionized water to a steam jacketed vessel and heating same to 60° C. 105.5 grams of a 32% active solution of tridecyl alcohol ether (4.2) sulfate are added with agitation and when the solution is clear 126.9 grams of a 29.6% active solution of Compound AA are added. 2.5 grams of polyethylene glycol 6000 distearate are then added with agitation until the solution is clear. The solution is then cooled to below 40° C. and 0.5 grams Dowicil 200, 1.5 grams benzyl alcohol and 0.4 grams fragrance are added. The pH is adjusted to 7.1 with 7.1 grams of 10% $H_3PO_4$ and the total mass is brought to 500 grams with the addition of deionized water to give a composition consisting of the following ingredients:

|  | wt/wt % |
|---|---|
| Compound AA | 7.512 |
| tridecyl alcohol ether 4.2 sulfate | 6.752 |
| polyethylene glycol | 0.500 |
| Dowicil 200 | 0.100 |
| benzyl alcohol | 0.300 |
| fragrance | 0.080 |
| $H_3PO_4$ | 0.142 |
| Polymer JR | 0.500 |
| deionized water | q.s. to 100% |

EXAMPLE II

A conditioning shampoo consisting of the following ingredients is prepared in accordance with the teachings of Example I:

|  | wt/wt % |
|---|---|
| lauric myristic imidazoline | 7.50 |
| Compound AA | 8.76 |

-continued

| | wt/wt % |
|---|---|
| stearyl triphosphate ester | 1.00 |
| propylene glycol | 1.00 |
| Dowicil 200 | 0.05 |
| benzyl alcohol | 0.10 |
| polyoxyethylene (80) sorbitan monolaurate | 2.00 |
| H$_3$PO$_4$ | 0.51 |
| fragrance | 0.50 |
| deionized water | q.s. to 100 |

The above composition is tested for foam volume and stability in accordance with the previously described modified Ross-Miles test and the following results are achieved:

| Foam Height Millimeters | |
|---|---|
| Initial | % Decay |
| 105 | 9.5 |

These results show a good initial foam which has a low decay level indicating a stable, rich, lasting foam.

EXAMPLE III

A shampoo composition consisting of the following ingredients is prepared in accordance with the teachings of EXAMPLE I:

| | wt/wt % |
|---|---|
| lauric myristic imidazoline | 4.00 |
| Compound AA | 1.10 |
| tridecyl alcohol ether (4.2) sulfate | 4.99 |
| polyoxyethylene (80) sorbitan monolaurate (70%) | 11.67 |
| polyethylene glycol (6000) distearate | 1.50 |
| Polymer JR | 0.40 |
| dye | 0.50 |
| Dowicil 200 | 0.10 |
| fragrance | 0.30 |
| deionized water | q.s. to 100 |

The above composition is tested for foam volume and stability in accordance with the previously described modified Ross-Miles test procedure and the following results are achieved.:

| Foam Height Millimeters | |
|---|---|
| Initial | % Decay |
| 112.5 | 15.3 |

The results indicate a good initial foam height and a stable, long-lasting foam.

The above composition is tested for eye irritancy in accordance with the procedure of the modified Draize test described above and found to be only a slight irritant.

EXAMPLE IV

A gel detergent and cleansing composition is prepared having the following formulation:

| | wt/wt % |
|---|---|
| Compound BB | 10.00 |
| sodium lauryl(3) ether sulfate | 5.00 |
| Compound AA | 2.00 |
| polyoxyethylene(80) sorbitan monopalmitate | 15.00 |
| Dowicil 200 | 0.10 |

-continued

| | wt/wt % |
|---|---|
| dye | 0.01 |
| fragrance | 0.30 |
| deionized water | q.s. to 100 |

EXAMPLE V

A detangling detergent composition is prepared having the following formulation:

| | wt/wt % |
|---|---|
| Compound CC | 15.00 |
| sodium lauryl(3) ether sulfate | 2.50 |
| C$_{14}$-C$_{16}$ olefin sulfonate | 5.00 |
| coconut monoethanolamide | 3.00 |
| Polymer JR | 1.00 |
| Dowicil 200 | 0.10 |
| dye | 0.01 |
| fragrance | 0.20 |
| deionized water | q.s. to 100 |

EXAMPLE VI

A conditioning shampoo composition is prepared having the following formulation:

| | wt/wt % |
|---|---|
| Compound DD | 5.00 |
| sodium lauryl sulfate | 15.00 |
| coconut monoalkanolamide | 2.50 |
| lauric diethanolamide | 2.00 |
| Dowicil 200 | 0.10 |
| dye | 0.01 |
| fragrance | 0.30 |
| deionized water | q.s. to 100 |

EXAMPLE VII

A liquid baby bath composition is prepared having the following formulation:

| | wt/wt % |
|---|---|
| lauric myristic imidazoline | 1.26 |
| tridecyl(100) ether sulfate | 3.42 |
| Compound CC | 4.50 |
| Dowicil 200 | 0.10 |
| benzyl alcohol | 0.30 |
| 1,23-bis[docosyl dimethyl ammonium] polyoxyethylene(7) dibromide | 1.10 |
| deionized water | q.s. to 100 |

Various other features and embodiments of the present invention not specifically enumerated will be obvious to those skilled in the art, all of which may be achieved without departing from the spirit and the scope of the invention as defined by the following claims. What is claimed is:

We claim:

1. A detergent and cleansing composition wherein the active ingredient consists essentially of from about 1.0 to 20.0 % by weight of the total composition of a compound of the formula

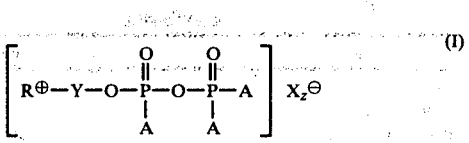

wherein
A is selected from —O, —OM and —O—Y—R with the proviso that at least one A is —O;
X is an anion;
z is an integer from 0 to 3;
R is an amidoamine moiety of the formula

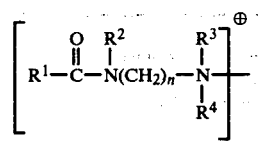

wherein:
$R^1$ is alkyl, alkenyl, alkoxy, or hydroxyalkyl of from 5 to 22 carbon atoms each, or aryl or alkaryl of up to 20 carbon atoms;
$R^2$ is hydrogen or alkyl, hydroxyalkyl or alkenyl of up to 6 carbon atoms each or cycloalkyl of up to 6 carbon atoms or polyoxyalkylene of up to 10 carbon atoms;
$R^3$ and $R^4$, which may be the same or different, are selected from alkyl, hydroxyalkyl, carboxyalkyl or up to 6 carbon atoms in each alkyl moiety, and polyoxyalkylene of up to 10 carbon atoms; in addition, $R^3$ and $R^4$ taken together with the nitrogen to which they are attached, may represent an N-heterocycle, in which the Y radical is bonded to a ring atom of said N-heterocycle other than the nitrogen of the R moiety;
n is an integer from 2 to 12;
Y is alkylene or alkylene interrupted by up to 3 oxygen atoms, of up to 12 carbon atoms, which alkylene chain may be substituted with lower alkyl, alkoxy, hydroxy or hydroxyalkyl, of not more than 10 carbon atoms each;
M is selected from the group of hydrogen, an organic radical selected from alkyl or hydroxyalkyl of up to 6 carbon atoms, polyhydroxyalkyl of up to 10 carbon atoms, cycloalkyl of up to 6 carbon atoms, aryl or arylalkyl of up to 10 carbon atoms, or a salt radical selected from alkali metals and alkaline earth metals.

2. The composition of claim 1 containing in addition at least one surfactant selected from the group consisting of anionic, nonionic, cationic and amphoteric surfactants wherein the amphoteric surfactant is selected from the group consisting of betaines, sultaines, phosphobetaines, phosphitaines, n-alkylamino propionates and n-alkylimino dipropionates and wherein the total active level of surfactants shall not exceed 35% by weight of the total composition.

3. The composition of claim 2 containing from about 1.0 to 20.0% by weight of the total composition of an anionic surfactant selected from the group consisting of alkylsulfate, alkylether sulfate, alkylmonoglyceryl ether sulfonate, alkylmonoglyceride sulfate, alkylmonoglyceride sulfonate, alkyl sulfonate, alkylaryl sulfonate, alkyl sulfosuccinate, alkyl sarcosinate, acyl isathionate, alkyl methyl tauride, fatty acid protein condensate and an alcohol ether carboxylate.

4. The composition of claim 2 containing from about 1.0 to 20.0% by weight of the total composition of a nonionic surfactant selected from the group consisting of alkylene oxide ethers of phenols, fatty alcohols, alkyl mercaptans, alkylene oxide esters of fatty acid amides, condensation products of ethylene oxide with partial fatty acid esters and mixtures thereof.

5. The composition of claim 2 containing from about 1.0 to 5.0% by weight of the total composition of a cationic surfactant selected from the group consisting of mono- and bis-quaternary ammonium halides, tertiary amine salts and cationic polymers.

6. The composition of claim 1 wherein said active ingredient is a compound of the formula:

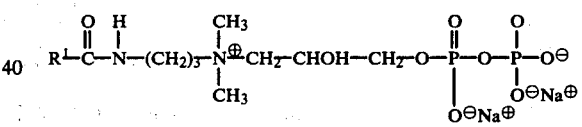

7. The composition of claim 1 wherein said active ingredient is a compound of the formula:

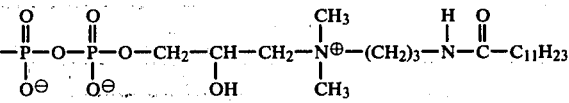

* * * * *